United States Patent
Lin (10) Patent No.: US 7,662,102 B2
(45) Date of Patent: Feb. 16, 2010

(54) METHOD OF MEASURING INSTANTANEOUS ARTERIAL BLOOD PRESSURE AND COMPLIANCE AND DEVICE THEREOF

(75) Inventor: Albert Chin-Yuh Lin, Taichung (TW)

(73) Assignee: E-Med Biotech, Inc., Taichung (TW)

(*) Notice: Subject to any disclaimer, the term of this patent is extended or adjusted under 35 U.S.C. 154(b) by 186 days.

(21) Appl. No.: 12/071,190

(22) Filed: Feb. 19, 2008

(65) Prior Publication Data

US 2009/0069699 A1    Mar. 12, 2009

(30) Foreign Application Priority Data

Sep. 12, 2007    (TW) ............................. 96134113 A (51) Int. Cl.
    *A61B 5/02*    (2006.01)
(52) U.S. Cl. ..................... 600/485; 600/486; 600/490
(58) Field of Classification Search ......... 600/485–486, 600/301, 306, 490
    See application file for complete search history.

(56) References Cited

U.S. PATENT DOCUMENTS

| 5,178,151 A | * | 1/1993 | Sackner ..................... 600/485 |
| RE34,663 E | * | 7/1994 | Seale ......................... 600/587 |
| 6,491,647 B1 | * | 12/2002 | Bridger et al. ............. 600/585 |
| 2004/0158163 A1 | * | 8/2004 | Cohen et al. ............... 600/508 |

OTHER PUBLICATIONS

Albert Chin-Yuh Lin, Huang-Nan Huang, Yi-Chang Su, Chih-Yuan Shiu, and Jui-Shan Lin, A New Noninvasive Approach to Detect the Artery's Pulsating Properties via Tissue Control Method, Aug. 23-26, 2007, Conference of the IEEE EMBS Cite, Internationale, Lyon, France, 2871-2874.*
Albert Chin-Yuh Lin, Huang-Nan Huang, Yi-Chang Su, Chih-Yuan Shiul, Yao-Horng Wang, Hao-Cheng Chiang, Hung Tungt and Jui-Shan Lin, On measuring the instantaneous blood pressure in an artery via the tissue control method, Jul. 30, 2007, Physiol Meas 28, 2007, 937-951).*

* cited by examiner

Primary Examiner—Charles A Marmor, II
Assistant Examiner—Michael D'Angelo
(74) Attorney, Agent, or Firm—Rosenberg, Klein & Lee (57) ABSTRACT

A method of measuring the instantaneous arterial blood pressure and compliance and the device thereof are disclosed. The method identifies a critical depth under the skin. At this critical position, the arterial mean blood pressure is equivalent to the mean blood pressure obtained on the skin. The variation in the arterial mean blood pressure is tracked and controlled to maintain the equivalence between the mean blood pressure measured on the skin and the arterial mean blood pressure. In this case, the compliance of the muscle tissues remains invariant. Therefore, the variation measured on the skin is simply the behavior of the blood vessel. Using the skin-artery correlation, the invention can obtain the instantaneous blood pressure after some computation and the dynamic compliance at the critical position.

8 Claims, 10 Drawing Sheets

FIG. 11

METHOD OF MEASURING INSTANTANEOUS ARTERIAL BLOOD PRESSURE AND COMPLIANCE AND DEVICE THEREOF

BACKGROUND OF THE INVENTION

1. Field of Invention

The invention relates to medical diagnosis and, in particular to a method of measuring the instantaneous arterial blood pressure in a non-invasive approach and the device thereof.

2. Related Art

Cardiovascular diseases have become one of the major death causes of human beings. Therefore, the study of blood vessel properties is one of the major medical research fields. The emphases have been on such behaviors as blood pressure, blood flow, and elasticity. The measurement of the instantaneous blood pressure of blood vessels is thus extremely important.

In 1876, Marey first invented the Sphygmograph to take the blood pressure. Afterwards, more researchers have devoted themselves in non-invasive, convenient and reliable equipment in order to take the arterial blood pressure in medical diagnosis and health care. Clinically, the blood pressure is almost measured using non-invasive intermittent techniques. The most common technique is to use auscultatory and computerized oscillometric method.

Later on, three non-invasive approaches have been proposed to measure the instantaneous intra-arterial blood pressure. The first is the employ the arterial tonometry based on coplanar measurement (Pressman et al. 1963 and Mackay et al. 1964). The second is the Peñáz's method (Peñáz's 1973 and Wesseling 1984, 1986). The third one is the volume-compensation method (Yamakoshi et al. 1979, 1980). The latter two are based upon the vascular unloading technique (Geddes 1970, Shirer 1962 and O'brien et al. 1991).

Current artery tonometrys include, for example, HDI CvProfilor (Cohn et al. 1995), Sphygmocor (Giot et al. 1996), Pulsepen (Salv et al. 2004), and Colin radial tonometry, all using the principle of arterial tonometry. In these cases, some artery of one arm is urged by a hard structure and partially compressed. Therefore, the pulsation waveform can be continuously read out without using an occluding cuff. However, to calibrate the obtained blood pressure measurement, one needs to use the auscultatory or cuff-oscillometric method to measure the systolic blood pressure (SBP), diastolic blood pressure (DBP), and mean blood pressure (MBP) of the other arm. The intra-arterial blood pressure is then estimated in proportion. Nonetheless, the transmission property of blood pressure from the artery to the skin above it is nonlinear.

The above-mentioned vascular unloading technique involves the Finapres type and the Portapres type, both performing continuous monitoring of the arterial blood pressure at fingers in a non-invasive approach. With the volume-clamp method disclosed by Peñáz, the finger arteries are clamped at a fixed diameter by applying an external pulsating pressure via an inflatable bladder mounted in a finger cuff and a fast-acting servo system. Finapres uses the Wesseling standard to determine a setpoint. The diameter of where the finger artery is clamped is determined by an infrared (IR) plethysmograph. The plethysmograph is disposed inside the finger cuff so that the transmural pressure is zero. At the same time, the cuff pressure is equal to the intra-arterial blood pressure. This equality assumes that the pulsating pressure has a diminishing loss from the artery to the cuff. Afterwards, Yamakoshi et. al. propose a volume-compensation method to improve the servo-reference and develop a local pressurization technique. These lead to a pad-type cuff sphygmomanometer for finger and wrist (Tanaka et al. 2005). Such a sphygmomanometer can prevent discomfort on the biological segment that is surrounded by the occluding cuff during a long-term measurement.

However, all the above-mentioned methods cannot obtain the true instantaneous blood pressure of the artery vessel. This is because these methods do not take into account the pressure transmission of the muscle tissues. Experience tells us that these conventional techniques cannot render accurate behaviors of arterial vessels.

The key issues are how to obtain the true instantaneous intra-arterial blood pressure and how to obtain characteristics of blood vessels such as the variation in their diameters. That is, it is desirable to obtain the simple variation of blood vessels. An objective of the invention is to employ a controlled method so that the muscle tissues are compliantly invariant, thereby rendering the simple behavior of blood vessel variations. At the same time, the characteristics of blood vessels are identified in order to estimate the arterial instantaneous blood pressure and its dynamic arterial dynamic compliance at the critical position.

SUMMARY OF THE INVENTION

An objective of the invention is to solve the above-mentioned problems by providing a method of measuring the instantaneous arterial blood pressure and compliance and the device thereof. At a specific position of skin, the behaviors between the muscle tissues and the arterial blood vessel are separated or decoupled. Thereby, the detection head can obtain purely the arterial vessel behaviors without the influence of the muscle tissues. Finally, the instantaneous arterial blood pressure and its dynamic compliance at the critical position are estimated in a non-invasive approach.

Another objective of the invention is to use the disclosed method and device to obtain the characteristics of arteries, such as the variation in their diameters, the instantaneous blood pressure, the mean blood pressure, the diastolic pressure, the systolic pressure, and the dynamic compliance at the critical position.

To achieve the above-mentioned objective, the measuring method disclosed herein includes the following steps:

a searching step: finding the critical depth $\bar{\lambda}_s$ when $\bar{P}_s = \bar{P}_b$ and determining $\bar{P}_s$ and $\bar{\lambda}_s$ using an actuator to impose a pressure on the skin, a pressure sensor to measure a skin mean blood pressure $\bar{P}_s$, and a displacement sensor to detect the depth $\lambda_s$ under the pressure, then using the pressure sensor to measure the peak-to-peak pressure value, where the above-mentioned procedure is repeated until the maximum peak-to-peak value is reached, with the corresponding depth being the critical depth $\bar{\lambda}_s$ and the mean blood pressure measured at the skin $\bar{P}_s$ being equal to the arterial mean blood pressure $\bar{P}_b$; wherein $\bar{P}_s$ is the mean blood pressure measured at the skin, $\bar{P}_b$ is the arterial mean blood pressure, and $\bar{\lambda}_s$ is the critical depth of the skin;

a controlling step: using the pressure sensor to monitor the blood pressure change transmitted from the artery to the skin $\Delta P_s$ when the arterial blood pressure changes by $\Delta P_b$ at the critical depth $\bar{\lambda}_s$, using the actuator to change the depressed depth of the skin for generating the corresponding displacement change $\Delta \lambda_s$ so that the blood pressure change at the skin $\Delta P_s$ approaches zero, in which case the muscle tissue compliance remain invariant, the tissue stiffness $K_t$ being equal to the tissue impedance $Z_t$ and thus making the mean blood pressure at the skin $\bar{P}_s$ and the arterial mean blood pressure $\bar{P}_b$ remain equivalent, where the displacement change $\Delta \lambda_s$ of the actuator detected by the displacement sensor is the variation in the arterial blood vessel diameter; wherein $\Delta P_b$ is the difference between the arterial blood pressure $P_b$ and the mean blood pressure $\overline{P}_b$, and $\Delta \lambda_s$ is the displacement change from the critical depth $\overline{\lambda}_s$ for the blood pressure change $\Delta P_b$;

an identifying step: simulating the artery vessel as a second-order system with mass, damping, and stiffness and performing system identification to obtain blood vessel parameters $M_v$, $D_v$, and $K_v$ as well as the artery impedance $Z_v$;

an estimating step: transmitting the detected signal to a controlling unit for computations, using the mean blood pressure at the skin $\overline{P}_s$, the artery impedance $Z_v$, and the arterial blood vessel diameter change $\Delta \lambda_s$ to estimate the arterial instantaneous blood pressure $\hat{P}_b$, and using the arterial instantaneous blood pressure $\hat{P}_b$ and the diameter displacement change $\Delta \lambda_v$ to make a plot of the arterial dynamic compliance at the critical position.

The invention also provides a measuring device in accord with the above-mentioned measuring method. The measuring device comprises: a detection head on the skin surface, including at least an actuator, a displacement sensor, and a pressure sensor; a controlling unit electrically coupled with the actuator, the displacement sensor, and the pressure sensor for signal analyses and processing; wherein the actuator is controlled by the controlling unit to depress the skin, the displacement sensor measures the depressed depth of the actuator and sends the displacement signal to the controlling unit for signal processing, and the pressure sensor detects the pressure signal on the skin and sends it to the controlling unit for signal processing.

BRIEF DESCRIPTION OF THE DRAWINGS

The invention will become more fully understood from the detailed description given herein below illustration only, and thus is not limitative of the present invention, and wherein:

FIG. 3b shows the impedance-equivalent physical models of FIG. 3a;

DETAILED DESCRIPTION OF THE INVENTION

The present invention will be apparent from the following detailed description, which proceeds with reference to the accompanying drawings, wherein the same references relate to the same elements.

The invention discloses a method of measuring the instantaneous arterial blood pressure and compliance as well as the measuring device thereof. They are used to study the pressure transmission properties from the arterial vessel to the skin, thereby estimating characteristics of arteries, such as its diastolic pressure, systolic pressure, mean blood pressure, instantaneous blood pressure, blood vessel diameters (i.e., the inner and outer diameters), thickness of blood vessel, and Young's coefficient. Such information can be used to make a plot of the dynamic compliance at the critical position for the artery.

The basic principle of the invention is as follows. A specific position of the skin is depressed until reaching a critical depth where the peak to peak pressure value is maximal. At this location, we provide continuously a pressure control to the blood vessels and muscle tissues under the skin. By the pressure control, the behaviors of blood vessels are isolated from the influence of muscle tissues. Such isolation is also called decoupling. Once the muscle tissues are decoupled, they behave like a rigid body. Therefore, when the pressure is transmitted from the artery to the skin, it is not affected by the tissues. The behaviors measured at the skin are thus purely from the artery, excluding the interference of muscle tissues.

Secondly, blood in the artery is continuously flowing. The intra-arterial blood pressure transmitted to the skin has a tiny variation at all times. The detection head disposed at the skin continuously monitors the blood pressure change at the skin. To take into account any possible compression or dilation of muscle tissues due to the blood pressure change, the detection head is used to moderately adjust the skin depression. This maintains the tissues as a rigid body, so that one can dynamically estimate the behaviors and characteristics of arteries.

Figure 1:
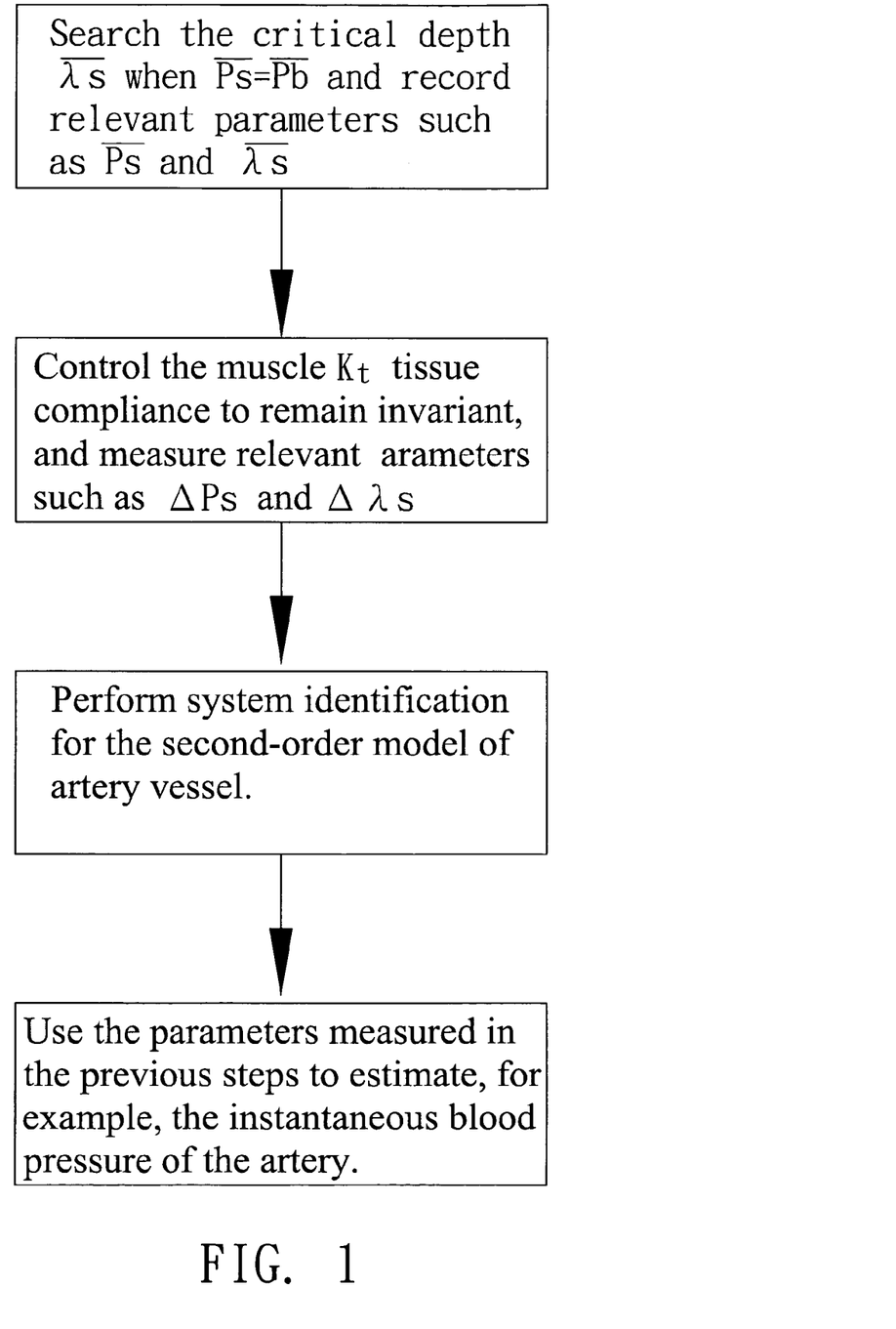
FIG. 1 is a flowchart showing the steps in the disclosed measuring method.
Figure 2:
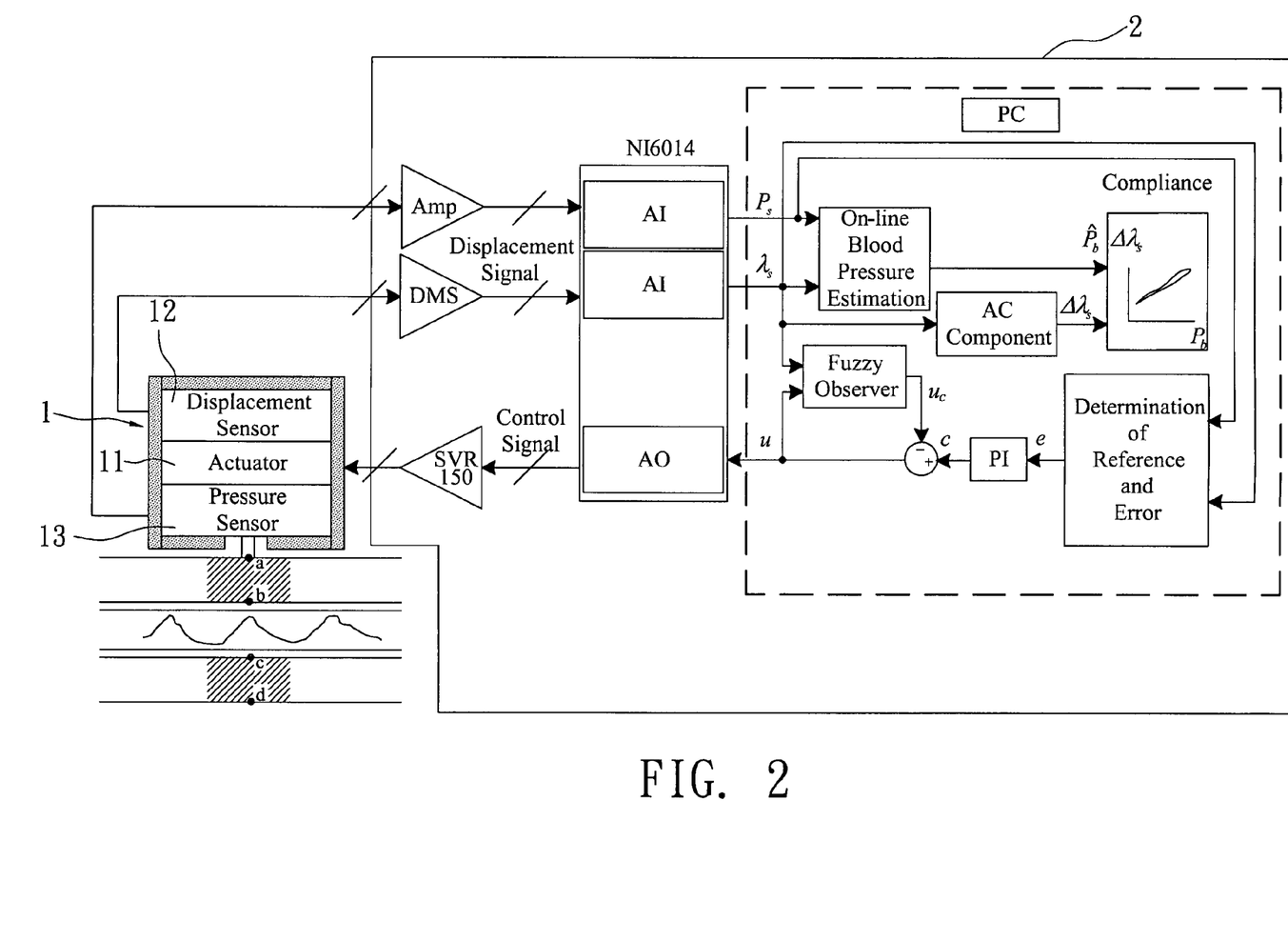
FIG. 2 is a schematic view of the disclosed measuring device.

Please refer to FIGS. 1 and 2. The method of measuring artery-related characteristics includes the following steps.

The searching step: Search a critical depth $\overline{\lambda}_s$ when $\overline{P}_s = \overline{P}_b$, and determine $\overline{P}_s$ and $\overline{\lambda}_s$, where $\overline{P}_s$ is the mean blood pressure measured at the skin surface, $\overline{P}_b$ is the arterial mean blood pressure, and $\overline{\lambda}_s$ is the critical depth of the depressed skin surface.

The search method is done by depressing the skin a depth using an actuator 11. A pressure sensor 13 measures the mean blood pressure at the skin $\overline{P}_s$. A displacement sensor 12 detects the depression depth $\lambda_s$ at this moment. The peak-to-peak pressure value is measured. Afterwards, the depression depth is adjusted. The above-mentioned procedure of measuring the skin mean blood pressure, the depression depth, and the peak-to-peak pressure value is repeated. The peak-to-peak pressure values at different depression depths are compared. The depth corresponding to the maximum peak-to-peak pressure is the critical depth $\overline{\lambda}_s$. At the critical depth $\overline{\lambda}_s$, the skin mean blood pressure $\overline{P}_s$ is equal to the arterial mean blood pressure $\overline{P}_b$. This is using the so-called depressing method to obtain the critical depth $\overline{\lambda}_s$.

The controlling step: The muscle tissue compliance is controlled to remain invariant. The control method is described as follows:

a. At the critical depth $\overline{\lambda}_s$, when the arterial blood pressure changes by $\Delta P_b$, the pressure sensor 13 is used to monitor the blood pressure change $\Delta P_s$ transmitted from the artery to the skin. The actuator 11 is used to change the depression depth of the skin, producing a corresponding displacement change $\Delta\lambda_s$ so that the blood pressure change at the skin $\Delta P_s$ approaches zero. When the pressure sensor detects that the pressure change at the skin $\Delta P_s$ is zero, the skin and the upper edge of the artery are moving up and down at the same time (i.e., the relative distance between them is invariant; com-moving). In this case, the compliance of the muscle tissues remains unchanged. That is, the tissue stiffness $K_t$ is equal to the tissue impedance $Z_t$. Thus, the arterial blood pressure change $\Delta P_b$ is not interfered by the tissues. The mean blood pressure at the skin $\overline{P}_s$ and the arterial mean blood pressure $\overline{P}_b$ remain equivalent. The displacement sensor 12 is used to detect the displacement change $\Delta\lambda_s$ of the actuator 11. The displacement change $\Delta\lambda_s$ is the change in the artery diameter $\Delta\lambda_v$. In particular, $\Delta P_b$ is the difference between the arterial blood pressure $P_b$ and the arterial mean blood pressure $\overline{P}_b$. $\Delta\lambda_s$ is the displacement produced by the actuator 11 for the blood pressure change $\Delta P_b$ and the critical depth $\overline{\lambda}_s$.

b. When the arterial mean blood pressure $\overline{P}_b$ varies by $\Delta\overline{P}_b$ so that the diameter of the arterial vessel changes. At the same time, the actuator 11 imposes a pressure opposite to the moving direction of the upper edge of the blood vessel (e.g., the point b of the blood vessel in FIG. 2). When the mean blood pressure $\overline{P}_b$ increases so that the blood vessel dilates, the actuator 11 increases the depression depth of the skin. On the other hand, when the arterial mean blood pressure $\overline{P}_b$ reduces so that the blood vessel contracts, the actuator 11 reduces the depression depth of the skin. By monitoring the mean blood pressure change at the skin $\Delta\overline{P}_b$ and waiting $\Delta\overline{P}_b$ to approach zero, the detection head on the skin can achieve a new critical position after the change. This makes the mean blood pressure at the skin $\overline{P}_s$ equal to the arterial mean blood pressure $\overline{P}_b$ again after the change.

The identifying step: Simulate the arterial blood vessel as a second-order system of mass, damping, and stiffness. Perform a system identification to obtain the blood vessel parameters $M_v$, $D_v$, and $K_v$, as well as the blood vessel impedance $Z_v$.

The estimating step: Transmit the detected signal to a controlling unit 2 for computations. The skin mean blood pressure $\overline{P}_s$, the blood vessel impedance $Z_v$, and the arterial blood vessel diameter change $\Delta\lambda_s$ are used to estimate the arterial instantaneous blood pressure $\hat{P}_b$. The arterial instantaneous blood pressure $\overline{P}_b$ and the displacement change in its diameter $\Delta\lambda_v$ are used to plot the arterial dynamic compliance at the critical position. The arterial characteristics measured using the disclosed method is dynamical.

As described above, the formula for computing the arterial blood vessel diameter change is $$\Delta\lambda_s = -1/Z_v \Delta P_b = \Delta\lambda_v$$

Besides, the formula used to estimate the arterial instantaneous blood pressure is $$\hat{P}_b = \overline{P}_b + \Delta P_b = \overline{P}_s - Z_v \Delta\lambda_s.$$

The compliance of arteries is obtained using $$C = \frac{d\lambda_s}{d\hat{P}_b}.$$

Please refer to FIG. 2 for a schematic view of the measuring device using the above-mentioned measuring method. The measuring device includes: a detection head 1 disposed on the skin and a controlling unit 2.

The detection head 1 consists of at least an actuator 11, a displacement sensor 12, and a pressure sensor 13. The controlling unit 2 is electrically coupled with the actuator 11, the displacement sensor 12, and the pressure sensor 13. The actuator 11 is controlled by the controlling unit 2 to impose a pressure on the skin. For example, it is used to depress the skin to reach the critical depth $\overline{\lambda}_s$. The displacement sensor 12 is used to detect the depression depth of the actuator 11. For example, it determines the depression depth $\lambda_s$, the critical depth $\overline{\lambda}_s$, and the displacement change $\Delta\lambda_s$. The displacement signal of the depression depth is transmitted to the controlling unit for signal processing.

The pressure sensor 13 is used to detect the pressure signal transmitted from the arteries inside to the skin surface. For example, the mean blood pressure at the skin $\overline{P}_s$ and the blood pressure change at the skin $\Delta P_s$ are measured. The pressure signals are transmitted to the controlling unit 2 for signal processing.

In this embodiment, the actuator 11 perform downward depression on the skin at the orders of millimeters (mm) and micrometers (μm). The mm-order depression is used for searching the critical depth $\overline{\lambda}_s$. The μm-order depression is used in accord with the displacement change $\Delta\lambda_s$ on the skin.

According to the embodiment, the displacement sensor is disposed on top of the actuator. The actuator is disposed on top of the pressure sensor. The pressure sensor urges against the skin using a detection head.

Theoretical Derivation of Above-Mentioned Measuring Method

Figure 3A:
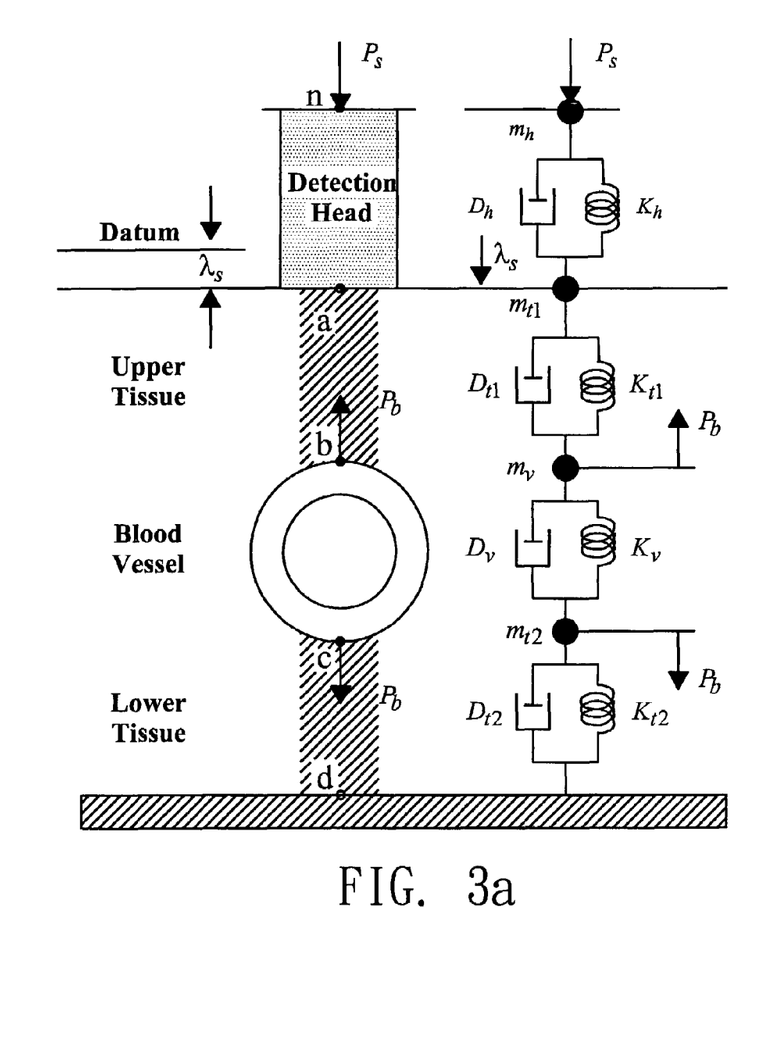
FIG. 3a shows the physical models for the upper and lower muscle tissues, skin, blood vessel, and bone in the invention.

FIG. 3a shows the physical models of arterial blood vessel and muscle tissues. The left-hand side of FIG. 3a shows, from top to bottom, the skin, upper tissue, arterial blood vessel, lower tissue, and bone, respectively. The skin is labeled by point a, the upper and lower edges of the arterial blood vessel are labeled by point b and point c, respectively. The bone is labeled by point d. The right-hand side of FIG. 3a shows the physical models simulating the upper tissue, arterial blood vessel, and lower tissue using mass, damping, and stiffness.

Here we assume that the motion model of an arterial blood vessel is collective. Therefore, we can use a mass unit M, a damping unit D, and a stiffness unit K to express the motion of each part from the skin to the bone. The motion behavior is caused by the force transmitted from the blood vessel to the skin due to the blood pressure. Suppose the force transmission from the blood vessel to the skin is equivalent to the pressure transmission. Then the mass unit M, the damping unit D, and the stiffness unit K of each part can be defined as:

$$M = P_m/\ddot{\lambda}; \quad D = P_d/\dot{\lambda}; \quad K = P_k/\lambda; \tag{1}$$

where P is the pressure and $\lambda$ is the displacement. Using the Laplace transform, the impedance Z of each part is defined as:

$$Z(s) = P/\lambda = Ms^2 + Ds + K \tag{2}$$

Figure 3B:
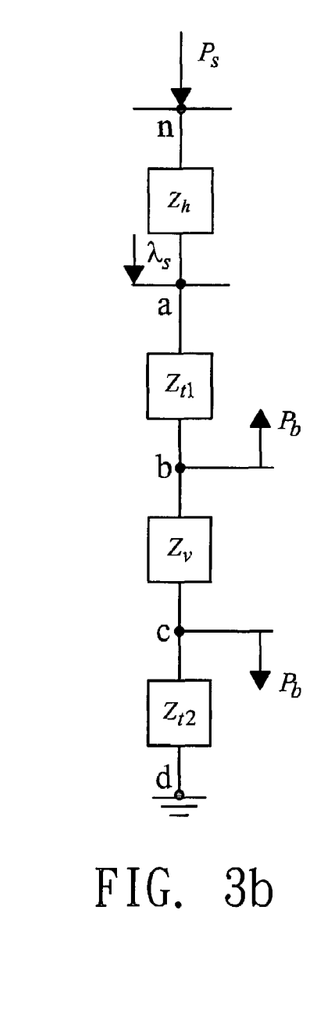

Please refer to FIGS. 3a and 3b. The subscripts h, t1, v, and t2 are used to represent the detection head, the upper tissue, the arterial blood vessel, and the lower tissue. Therefore, the symbols $Z_h$, $Z_{t1}$, $Z_v$, and $Z_{t2}$ represent the impedance of the corresponding part in the above collective model.

Figure 3C:
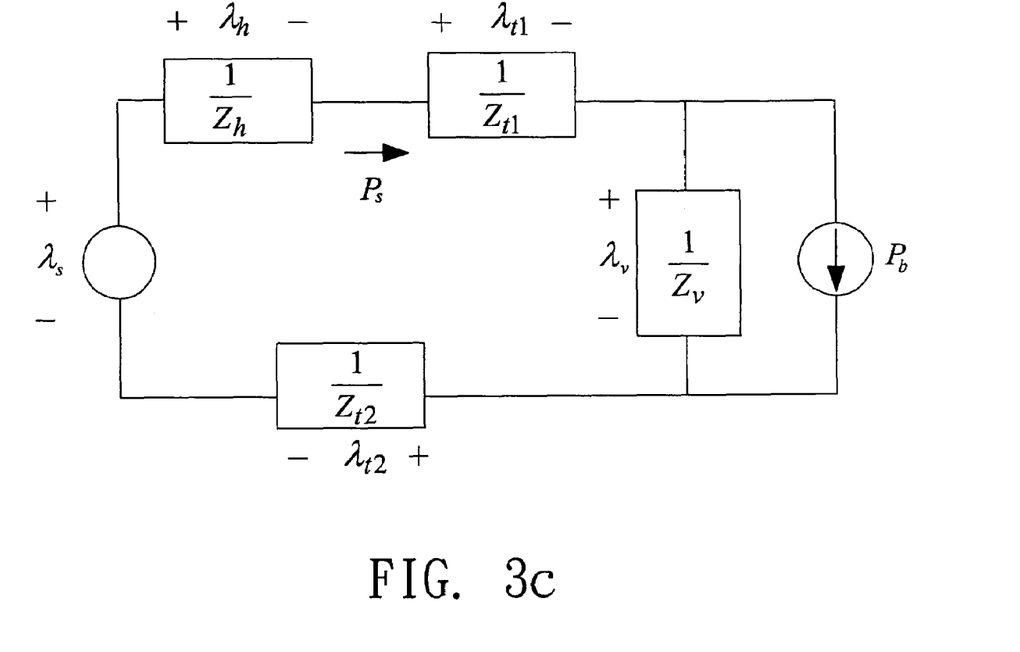
FIG. 3c shows the equivalent mechanical circuit models of FIG. 3b.

Furthermore, if the above-mentioned displacement λ is simulated by a voltage and the pressure P by an electrical current, then the arterial blood pressure can be expressed using an equivalent mechanical circuit model, where the mechanical impedance is analogous to the electrical admittance. FIG. 3c shows the equivalent mechanical circuit model of the transmission of blood pressure from the artery to the skin. Afterwards, the impedance of the detection head $Z_h$ and the impedances of the upper and lower tissues $Z_{t1}$, $Z_{t2}$ are combined to have the total impedance $Z_t$, simplifying the original circuit model to the one in FIG. 3d. Explicitly, $$1/Z_t = 1/Z_h + 1/Z_{t1} + 1/Z_{t2}. \quad (3)$$

Figure 3D:
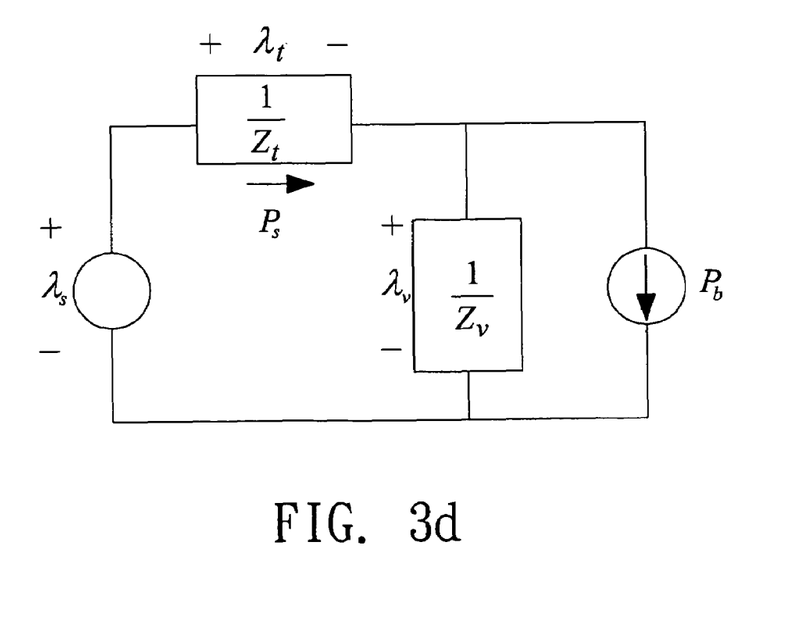
FIG. 3d shows the simplified mechanical circuit models of FIG. 3c.

The above-mentioned detection head can be a cuff with a pneumatic servo or an artery tonometry with a piezo-actuator. If the detection head is an artery tonometry with a piezo-actuator, the impedance of the detection head can be ignored in comparison with that of the muscle tissues. In the case of a cuff with a pneumatic servo, the impedance of the detection head has to be taken into account. Moreover, the impedances of the muscle tissues and blood vessels are not constant. They vary with the depression depth.

In FIG. 3d, the blood pressure at the skin $P_s$ is caused by the depression depth $\lambda_s$ and the arterial blood pressure $P_b$. It can be expressed as:

$$P_s = [Z_t Z_v/(Z_t + Z_v)]\lambda_s + [Z_t/(Z_t + Z_v)]P_b. \quad (4)$$

Since the arterial blood pressure $P_b$ is the sum of the arterial mean blood pressure $\overline{P}_b$ (DC part) and the arterial blood pressure change $\Delta P_b$ (AC part), it is possible to decompose the arterial blood pressure into its DC and AC parts, as detailed below.

(1) Effects and influences of the DC part on the arterial blood pressure. Please refer to FIG. 4. When the skin is depressed to a critical depth $\overline{\lambda}_s$ (using the depressing method), the mean blood pressure measured at the skin surface $\overline{P}_s$ is equal to the mean blood pressure $\overline{P}_b$. Eq. (4) can thus be rewritten as $$\overline{P}_s = [\overline{Z}_t \overline{Z}_v/(\overline{Z}_t + \overline{Z}_v)]\overline{\lambda}_s + [\overline{Z}_t/(\overline{Z}_t + \overline{Z}_v)]\overline{P}_b. \quad (5)$$

Figure 4:
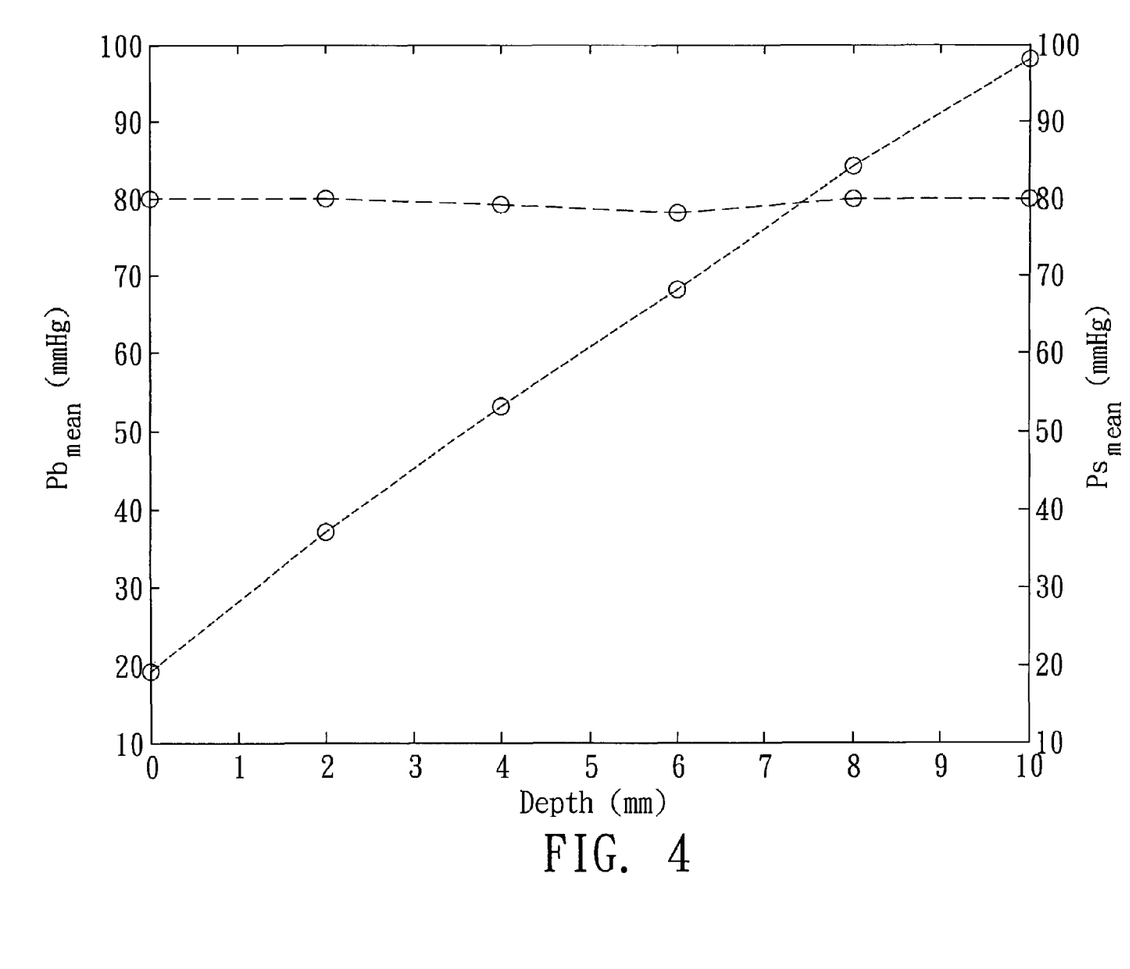
FIG. 4 shows the blood pressure measured at the skin surface and the arterial mean blood pressure for different depression depths, where they become equal at the critical depth.

Inserting $\overline{P}_s = \overline{P}_b$ into Eq. (5), one obtains $$\overline{Z}_s = (\overline{P}_s/\overline{\lambda}_s) = \overline{Z}_t = K_t. \quad (6)$$

Obviously, Eq. (6) shows that at the critical position $\overline{\lambda}_s$ (i.e., where $\overline{P}_s = \overline{P}_b$), the stiffness measured at the skin surface is equal to the stiffness of the muscle tissues and the detection head $K_t$ only, excluding the stiffness of blood vessel $K_v$.

(2) Effects and influences of the AC part on the arterial blood pressure. When the AC part of the arterial blood pressure is imposed on the DC part of the arterial blood pressure at the critical position $\overline{\lambda}_s$, Eq. (4) can be rewritten as $$\overline{P}_s + \Delta P_s = (Z_t Z_v/(Z_t + Z_v))(\overline{\lambda}_s + \Delta \lambda_s) + Z_t/(Z_t + Z_v)(\overline{P}_b + \Delta P_b) \quad (7)$$

Plugging Eq. (6) and $\overline{P}_s = \overline{P}_b$ into Eq. (7), one obtains $$\Delta P_s = (Z_t Z_v/(Z_t + Z_v))(1 - K_t/Z_t)\overline{\lambda}_s + \quad (8)$$
$$(Z_t Z_v/(Z_t + Z_v))\Delta \lambda_s + Z_t/(Z_t + Z_v)\Delta P_b$$

If an opposite pressure $\Delta P_s$ is imposed so that the displacement of the actuator at the critical depth $\overline{\lambda}_s$ is invariant and the displacement change $\Delta \lambda_s$ measured at the skin remains zero, then Eq. (8) becomes $$\Delta P_s = Z_t/(Z_t + Z_v)\Delta P_b + (Z_t Z_v/(Z_t + Z_v))(1 - K_t/Z_t)\overline{\lambda}_s. \quad (9a)$$

The idea of Eq. (9a) is analogous to the Peñáz's method or the volume-compensation method in the prior art. These methods maintain the cuff volume by providing an opposite pressure $\Delta P_s$ to the arterial mean blood pressure.

In these methods, the Wesseling criteria or the volume compensation method is employed to minimize the measured errors. However, to minimize or even completely eliminate the errors is extremely difficult or impossible. This is because either method cannot truly identify the impedances of the muscle tissues and blood vessel during the pulsation. In the conventional volume control methods, the muscle tissues and the blood vessel are coupled together. No separation is made to the system. Therefore, the conventional techniques cannot accurately obtain the information due to the arterial behaviors.

ADVANTAGES OF THE INVENTION

As described above, the invention makes improvements in the problems of the prior art and obtains satisfactory effects. In particular, the depression depth $\Delta \lambda_s$ is adjusted by moving the actuator up and down, so that the blood pressure change at the skin $\Delta P_s$ is zero. This is used to maintain the mean blood pressure $\overline{P}_s$. Under this mean blood pressure $\overline{P}_s$, the impedances of the muscle tissues and the detection head are kept the same. That is, $Z_t = K_t$. Eq. (8) thus becomes $$\Delta \lambda_s = -1/Z_v \Delta P_b = \Delta \lambda_v, \quad (9b)$$

where $\Delta \lambda_v$ is the change of the blood vessel diameter.

Eq. (9b) shows the displacement change in the diameter of blood vessel under the arterial blood pressure as measured at the skin surface. The most important meaning is that the pulsating behavior of the artery can be decoupled from the muscle tissues and the detection head. This means that its behavior mode can be independently singled out for observation. Using this method, it is possible to identify the blood vessel impedance and further estimate the intra-arterial blood pressure.

That is, a control method is used to maintain the equality between the pressure measured at the skin and the arterial mean blood pressure (i.e., $\overline{P}_s = \overline{P}_b$). The muscle tissues are maintained at the same stiffness such that $Z_t = K_t$. The muscle tissues and the detection head can be considered as a rigid body. At the same time, the motion behavior measured at the skin is simply related to the motion behavior of the blood vessel. Therefore, it is possible to obtain characteristics of arterial blood vessels, such as the variation in the blood vessel diameter, the instantaneous arterial blood pressure, and its dynamic compliance.

Tissue Control Method

As described above, to obtain the situation given in Eq. (9b), the invention provides a Tissue Control Method (TCM) to detect the variation in the diameter of arterial blood vessel and the instantaneous arterial blood pressure.

More explicitly, the TCM tracks the variation of the arterial blood pressure at the critical position where the stiffness of the muscle tissues and the detection head remain invariant.

Based upon Eqs. (6) and (7), the control graph of the TCM is indicated in FIG. 5, where $G_c$ refers to the controller and the actuator.

Variation in The Blood Vessel Diameter Being The Actuator Displacement

Figure 5:
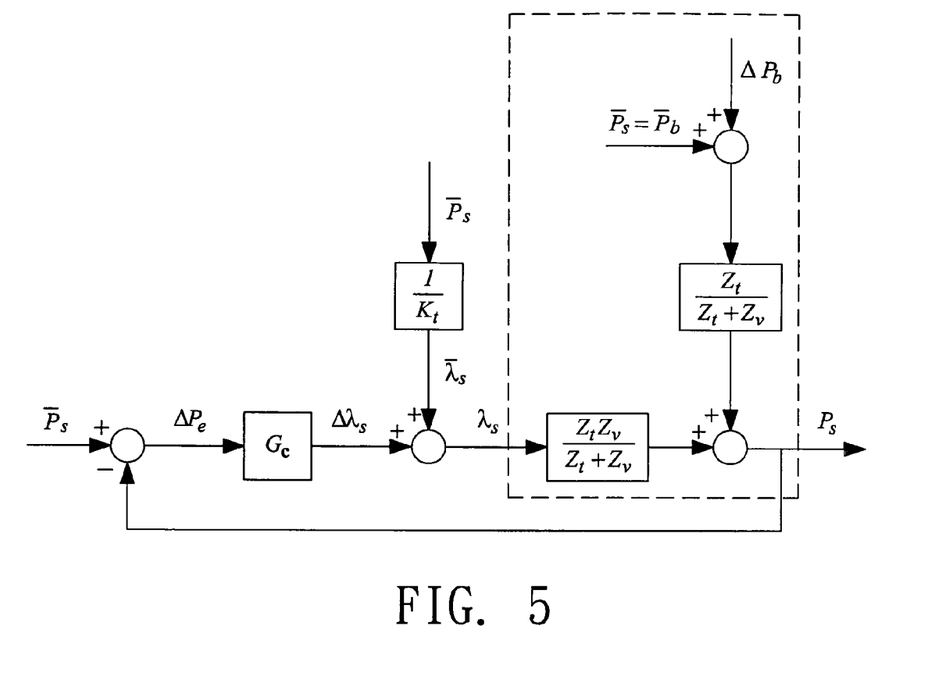
FIG. 5 is a control diagram of the disclosed TCM, showing the control over the stimulation produced by the mean blood pressure and the arterial blood pressure change at the critical depth.

The system response $P_s$ in FIG. 5 is the result under the actions of $\overline{P}_s$ and $\Delta P_b$. We can analyze individual effects of $\overline{P}_s$ and $\Delta P_b$. In the following, we analyze the effects of the mean blood pressure at the skin and the change in the arterial blood pressure to the system response.

Discussions of System Response Caused by Mean Blood Pressure—DC Effects

Figure 6:
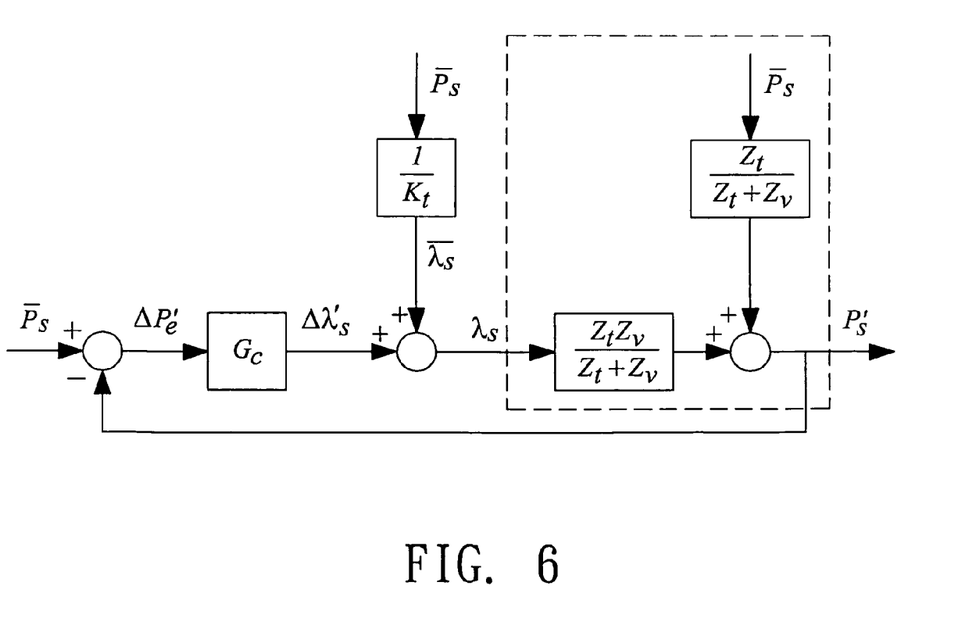
FIG. 6 is a control diagram when the arterial mean blood pressure produces a stimulation.

FIG. 6 is the control diagram of maintaining the arterial mean blood pressure. It indicates the effects of the mean blood pressure measured at the skin $\overline{P}_s$ to the system response. FIG. 6 shows the effects when the controlling unit is only affected by the mean blood pressure $\overline{P}_s$. In this case, an appropriately selected controller can diminish the error signal $\Delta P'_e$ in the stable state. Thus, the system response $P'_s = \overline{P}_s$ with $$P'_s[Z_tZ_v/(Z_t+Z_v)](1/K_t)\overline{P}_s + [Z_t/(Z_t+Z_v)]\overline{P}_s = \overline{P}_s, \quad (10)$$

and $$Z_t = K_t, \quad (11)$$
$$\text{and } \Delta\lambda'_s = 0, \lambda_s = \overline{\lambda}_s.$$

The above description means that when the TCM is used, the stiffness measured at the skin surface is only the total stiffness of the muscle tissues and the detection head, excluding the stiffness of the blood vessel. That is, when TCM is used for controlling at the critical depth, the stiffness of the muscle tissues can be kept invariant.

Figure 7:
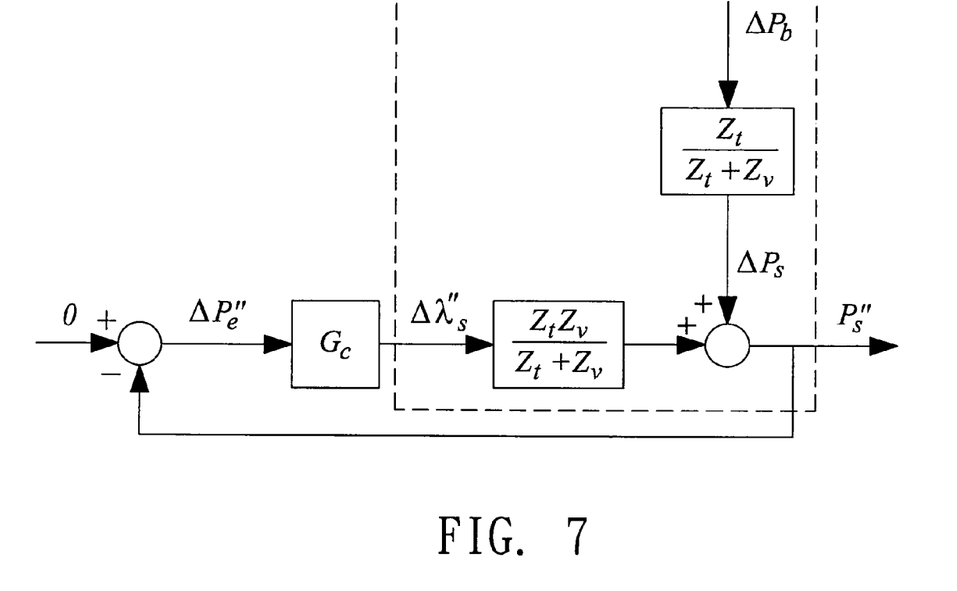
FIG. 7 is a control diagram when the arterial blood pressure change produces invention stimulation.

Discussions of System Response Caused by Variation of Arterial Blood Pressure—AC Effects FIG. 7 shows the effects of the change of arterial blood pressure $\Delta P_b$ on the system response. The system tends to maintain the mean blood pressure in a control sense. To achieve this objective, by moving up and down the displacement $\Delta\lambda''_s$ of the skin, it is possible to track the arterial blood pressure change $\Delta P_b$. An appropriate control algorithm is designed so that the system response $P'''_s$ vanishes in the stable state, i.e., $$P''_s = [Z_t/(Z_t+Z_v)]\Delta P_b + [Z_tZ_v/(Z_t+Z_v)]\Delta\lambda''_s = 0, \quad (12)$$

Then Eq. (12) gives $$\Delta\lambda_s = \Delta\lambda''_s = -(1/Z_v)\Delta P_b = \Delta\lambda_v. \quad (13)$$

Eq. (13) is the same as Eq. (9b). This shows that the variation of the blood vessel diameter $\Delta\lambda_s$ ($\Delta\lambda''_s$) can be measured at the skin surface.

More explicitly, the above derivations clearly point out that the arterial blood vessels can be individually identified, providing other blood vessel-related information such as the impedance. Therefore, to obtain the blood vessel impedance $Z_v$, it is necessary to derive a system equation using observable signals $\Delta P'''_e$ and $\Delta\lambda''_s$ for system identifications.

Obtaining Instantaneous Arterial Blood Pressure by Tracking Blood Pressure

According to the TCM, the purpose of the control algorithm is to maintain the stiffness of the muscle tissues invariant when the mean blood pressure is affected. This can simplify the motion behavior of blood vessels as the blood pressure varies. As a result, purely blood vessel behaviors are obtained. By identifying the blood vessel impedance, the instantaneous arterial blood pressure and the dynamic compliance of artery can be estimated.

Identification of Blood Vessel Impedance

To identify the blood vessel impedance $Z_v$, it is necessary to derive an identifiable system. In FIG. 7, the error signal $\Delta P'''_e$ is the tracking signal of $\Delta P_s$. The system response $$P''_s = -\Delta P''_e = \frac{Z_t}{Z_t+Z_v}\Delta P_b + \frac{Z_tZ_v}{Z_t+Z_v}\Delta\lambda''_s \quad (14)$$

and $$\Delta P_s = \frac{Z_t}{Z_t+Z_v}\Delta P_b = -(\hat{G}_c+1)\Delta P''_e. \quad (15)$$

Here $\hat{G}_c$ is a designed open-circuit gain. Using the calibration of a controller, the effect of the transfer function $Z_tZ_v/(Z_t+Z_v)$ is almost canceled.

Inserting Eqs. (11) and (15) into Eq. (14), we obtain $$\frac{K_tZ_v}{K_t+Z_v}\Delta\lambda''_s = \hat{G}_c\Delta P''_e. \quad (16)$$

Using the parameters $M_v$, $D_v$, and $K_v$ in the following equation (17), one can identify the blood vessel impedance $Z_v$:

$$(M_vs^2 + D_vs + K_v)\Delta\overline{\lambda}_s = \Delta\tilde{P}_e; \quad (17)$$

$$\Delta\tilde{P}_e = \hat{G}_c\Delta P''_e; \Delta\tilde{\lambda}_s = \Delta\lambda''_s - (1/K_t)\Delta\tilde{P}_e. \quad (18)$$

Estimation of Instantaneous Arterial Blood Pressure

After the blood vessel impedance $Z_v$ is identified using Eq. (17), Eq. (19) below can be derived using Eq. (9b). This formula can be used to estimate the instantaneous arterial blood pressure:

$$\hat{P}_b = \overline{P}_b + \Delta P_b = \overline{P}_s - Z_v\Delta\lambda_s. \quad (19)$$

Computation of Arterial Dynamic Compliance at the Critical Position

The arterial dynamic compliance at the critical position is defined by $$C = [d(\Delta\lambda_s)/d\hat{P}_b]|_{\overline{P}_b=\overline{P}_s}. \quad (20)$$

The important thing here is that the obtained compliance is purely the pulsating behavior of the artery. The influences of muscle tissues and detection head are not included. Consequently, the disclosed TCM is the unique method that utilizes the decoupling concept and is obviously superior to the methods in the prior art.

When $\overline{P}_b = \overline{P}_s$, the muscle tissues do not affect the pressure transmission from the blood vessel to the skin. As long as the depression depth for $\overline{P}_b = \overline{P}_s$ is found, related control means can be employed to control the motion behaviors between the muscle tissues and the arterial blood vessel. Characteristics of an artery are thus obtained during its dynamic state.

Discussions of Change in Arterial Mean Blood Pressure and Effects of Tracking and Controlling It The above description already shows that the TCM can effectively control the compliance of muscle tissues for the later estimation of arterial behaviors. To obtain more accurate arterial blood vessel characteristics, such as the instantaneous arterial blood pressure, the effects of the change in arterial mean blood pressure $\Delta \overline{P}_b$ is further controlled.

Figure 8:
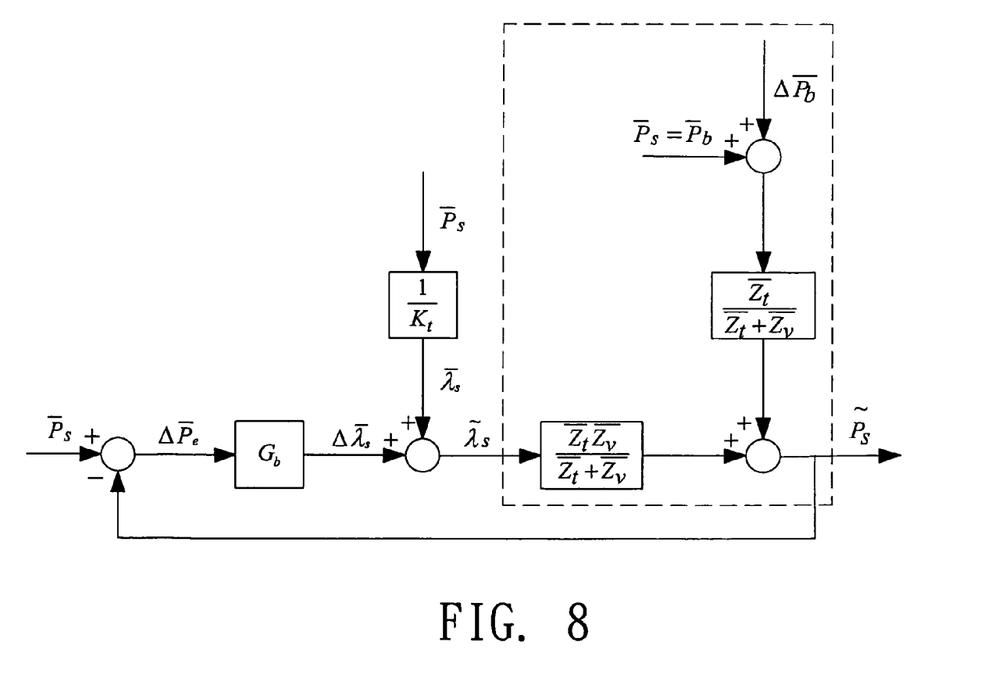
FIG. 8 is a control diagram of tracking the arterial mean blood pressure according to the invention.

Please refer to FIG. 8. It is schematic tracking plot when the arterial mean blood pressure $\Delta \overline{P}_b$ is taken into account. $G_b$ is the transfer function of the controller and the actuator.

Using an appropriate controller, the error signal $\Delta \overline{P}_e$ can approach zero in the stable state. In this case, the system response $\tilde{P}_s = \overline{P}_s$. Thus, $$\tilde{P}_s = [\overline{Z}_t \overline{Z}_v / (\overline{Z}_t + \overline{Z}_v)](\overline{\lambda}_s + \Delta \overline{\lambda}_s) + [\overline{Z}_t / (\overline{Z}_t + \overline{Z}_v)](\overline{P}_s + \Delta \overline{P}_b) = \overline{P}_s \quad (21)$$

Inserting Eq. (6) and $\overline{Z}_t = K_t$, $\overline{Z}_v = K_v$ into Eq. (21), one obtains $$\Delta \overline{\lambda}_s = -1 / K_v \Delta \overline{P}_b = \Delta \overline{\lambda}_v. \quad (22)$$

Observing Eq. (22), one realizes that the displacement measured on the skin surface is caused by the variation in arterial mean blood pressure. This displacement change at the skin is the diameter change $\Delta \overline{\lambda}_v$ of the arterial blood vessel. Therefore, a new critical depth can be obtained by tracking the arterial mean blood pressure change $\Delta \overline{P}_e$ and controlling the depression depth. In this case, the transmural stress of blood vessel is zero. That is, the arterial mean blood pressure and the mean blood pressure measured at the skin remain equivalent.

Figure 9:
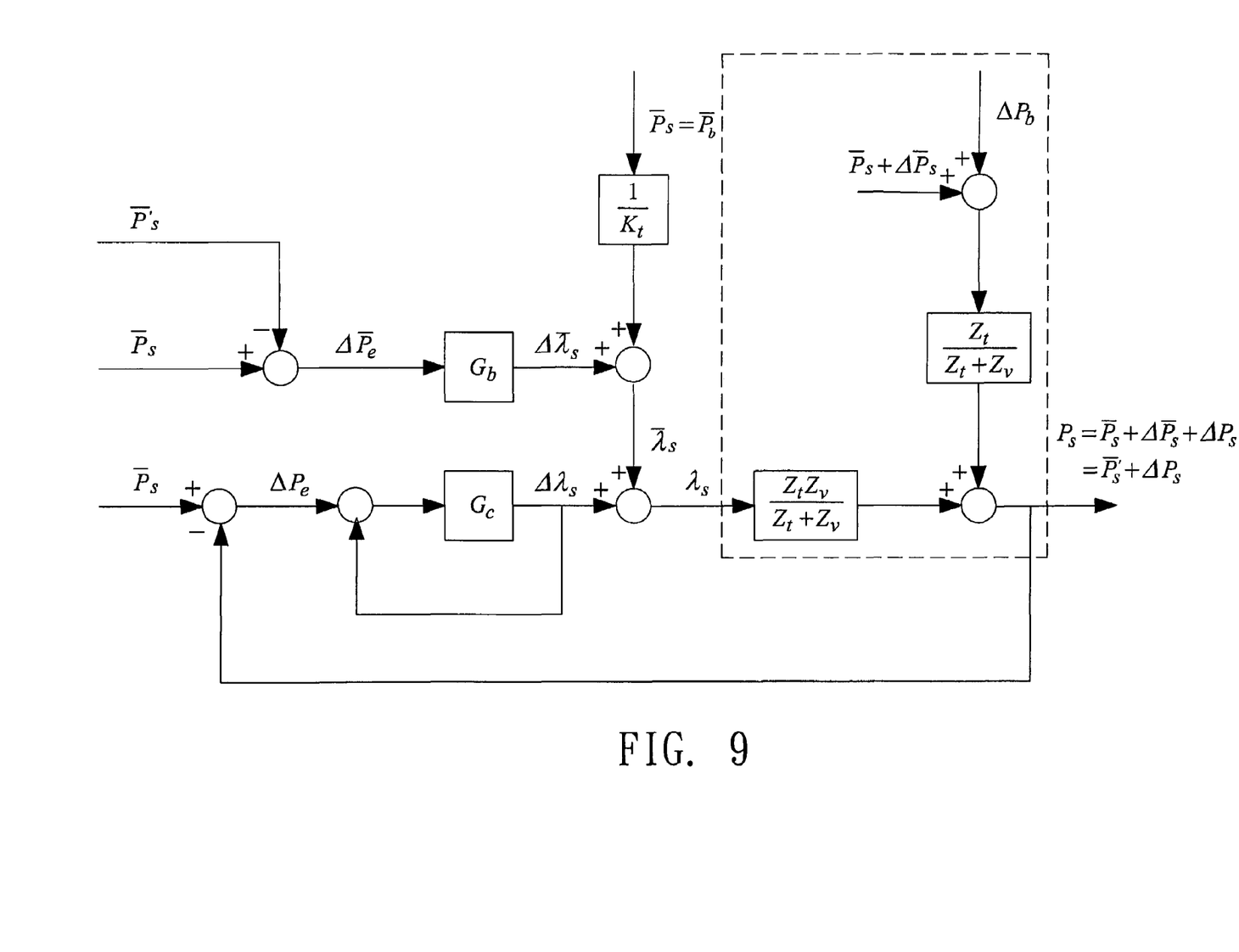
FIG. 9 shows the complete TCM control diagram for tracking the arterial mean blood pressure and the arterial mean blood pressure change.

FIG. 9 is the TCM control block diagram according to the invention. The system is used to track the arterial mean blood pressure and the arterial blood pressure change. It is more suitable when the arterial mean blood pressure has a large variation. The precision of the invention is thus increased.

Figure 10:
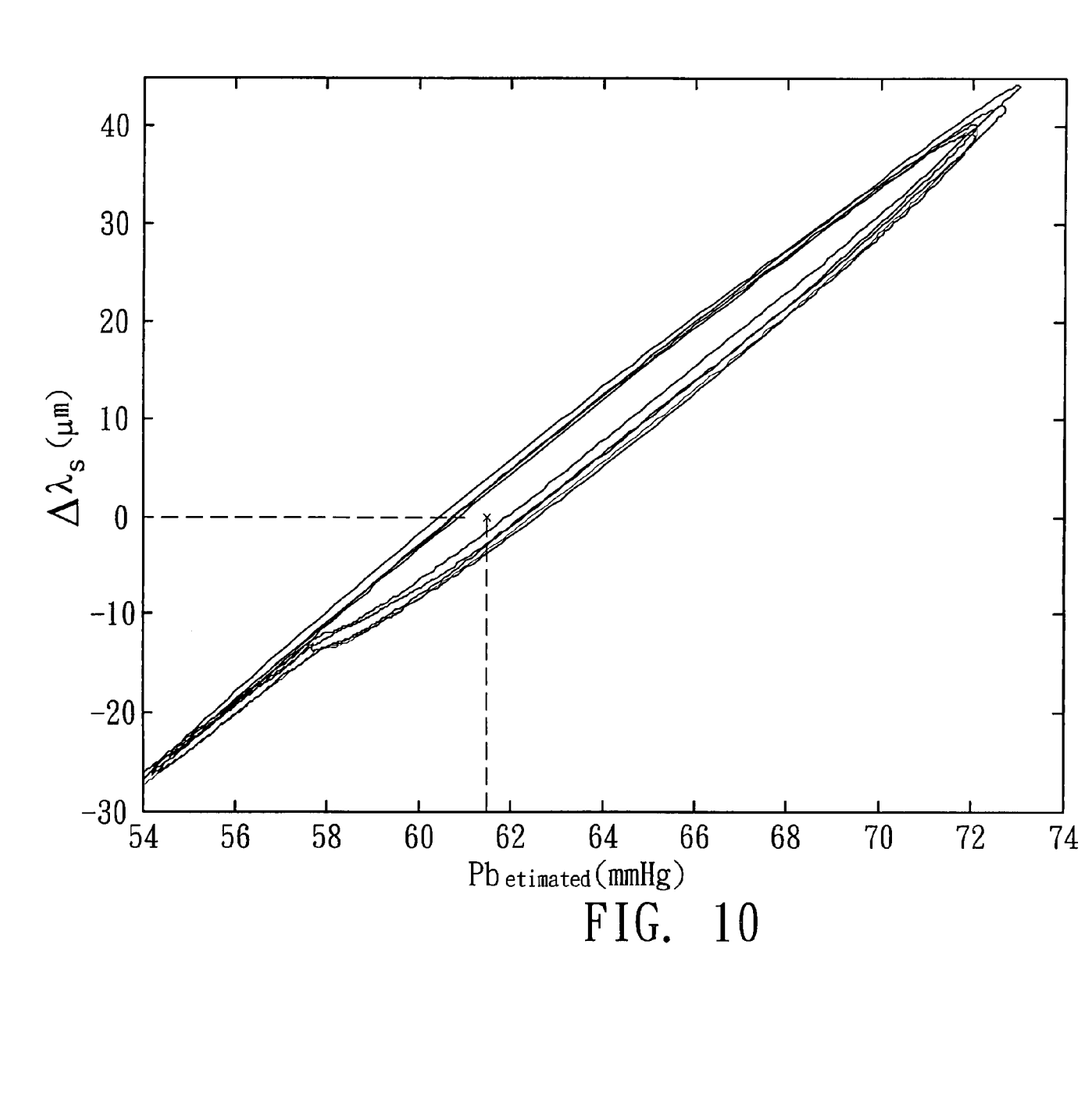
FIG. 10 shows the estimated hysteresis phenomenon of the arterial blood pressure and the blood vessel diameter change in five cycles of the SBP and DBP.
Figure 11:
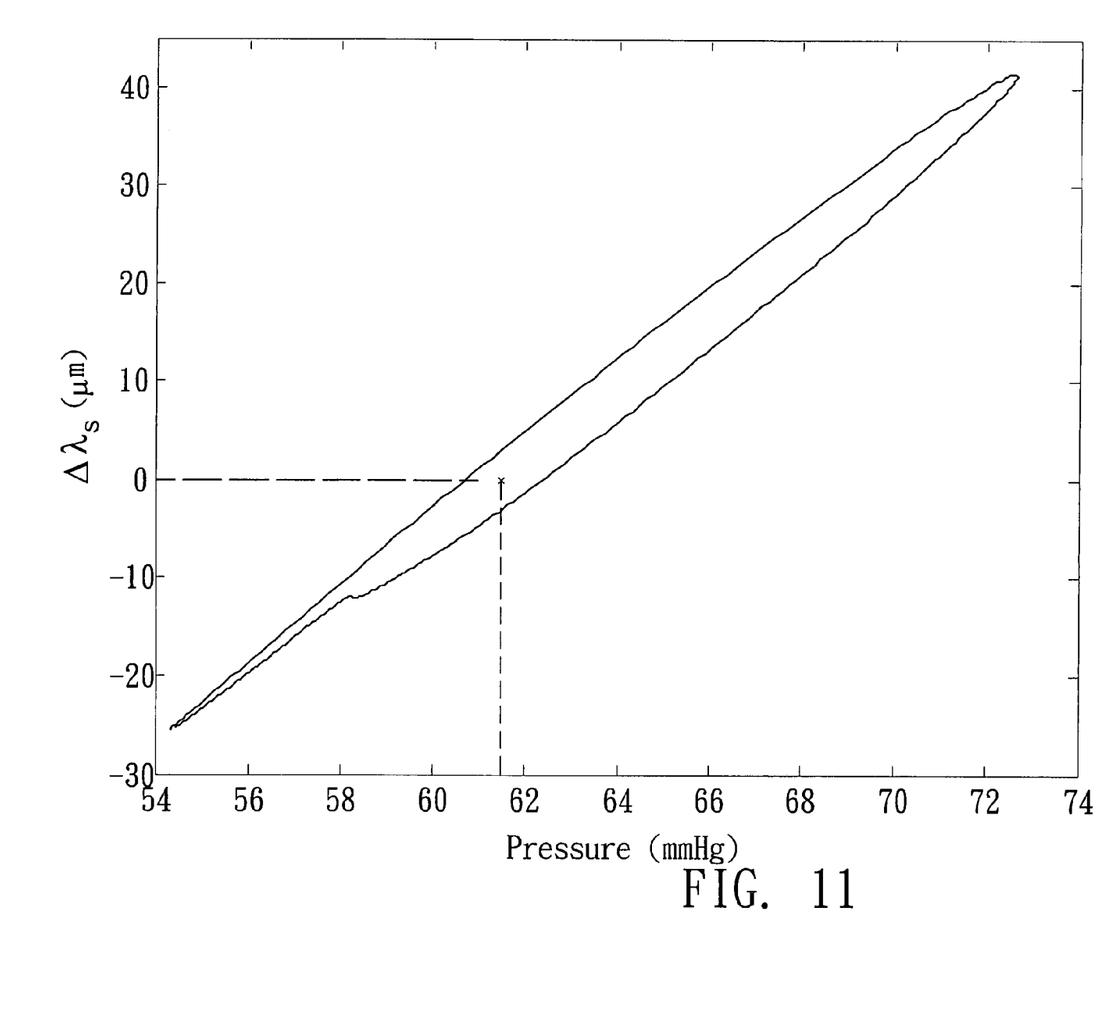
FIG. 11 shows the estimated hysteresis phenomenon of the arterial blood pressure and the blood vessel diameter change in fourteen cycles of the SBP and DBP, and shows the dynamic compliance at the critical position of the artery.

Moreover, after knowing the displacement change in the arterial diameter $\Delta \lambda_s$ and the instantaneous arterial blood pressure $\hat{P}_b$ obtained from related calculations, it is possible to plot the dynamic compliance of the arterial blood vessel at the critical position. Such a plot (e.g., FIG. 10 and FIG. 11) has a very high medical value in diagnosis. In particular, FIG. 10 shows the estimated hysteresis phenomenon of the arterial blood pressure and the blood vessel diameter change during five cycles of the SBP and DBP. FIG. 11 shows the estimated mean hysteresis phenomenon of the arterial blood pressure and the blood vessel diameter change during fourteen cycles of the SBP and DBP. This plot also shows the dynamic compliance when the artery is at its critical position.

In summary, the measuring method and device of the invention measure and control the arterial signals on the skin in a non-invasive approach, and estimate through some calculations such arterial characteristics as the instantaneous blood pressure, mean blood pressure, SBP, DBP, and arterial dynamic compliance at the critical position. The change in the diameter of arterial blood vessel can also be obtained. The changes in the volume and flux of the artery can also be obtained in this way. Moreover, the invention has very accurate estimates in the arterial characteristics. Therefore, it has a high medical value.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A method for measuring the arterial instantaneous blood pressure and compliance, comprising:

a searching step: finding the critical depth $\overline{\lambda}_s$ when $\overline{P}_s = \overline{P}_b$ and determining $\overline{P}_s$ and $\overline{\lambda}_s$ using an actuator to impose a pressure on the skin, a pressure sensor to measure a skin mean blood pressure $\overline{P}_s$, and a displacement sensor to detect the depth $\lambda_s$ under the pressure, then using the pressure sensor to measure the peak-to-peak pressure value, where the above-mentioned procedure is repeated until the maximum peak-to-peak value is reached, with the corresponding depth being the critical depth $\overline{\lambda}_s$ and the mean blood pressure measured at the skin being equal to the arterial mean blood pressure $\overline{P}_b$; wherein $\overline{P}_s$ is the mean blood pressure measured at the skin, $\overline{P}_b$ is the arterial mean blood pressure, and $\overline{\lambda}_s$ is the critical depth of the skin;

a controlling step: using the pressure sensor to monitor the blood pressure change $\Delta P_s$ transmitted from the artery to the skin when the arterial blood pressure changes by $\Delta P_b$ at the critical depth $\overline{\lambda}_s$, using the actuator to change the depressed depth of the skin for generating the corresponding displacement change $\Delta \lambda_s$ so that the blood pressure change at the skin $\Delta P_s$ approaches zero, in which case the muscle tissue compliance remain invariant, the tissue stiffness $K_t$ being equal to the tissue impedance $Z_t$ and thus making the mean blood pressure at the skin $\overline{P}_s$ and the arterial mean blood pressure $\overline{P}_b$ remain equivalent, where the displacement change $\Delta \lambda_s$ of the actuator detected by the displacement sensor is the variation in the arterial blood vessel diameter; wherein $\Delta P_b$ is the difference between the arterial blood pressure and the mean blood pressure, $\Delta \lambda_s$ is the displacement change from the critical depth $\overline{\lambda}_s$ for the arterial mean blood pressure change of $\Delta P_b$;

an identifying step: simulating the artery vessel as a second-order system with mass, damping, and stiffness and performing system identification to obtain blood vessel parameters $M_v$, $D_v$, and $K_v$ as well as the artery impedance $Z_v$;

an estimating step: transmitting the detected signal to a controlling unit for computations, using the mean blood pressure at the skin $\overline{P}_s$, the artery impedance $Z_v$, and the arterial blood vessel diameter change $\Delta \lambda_s$ to estimate the arterial instantaneous blood pressure $\hat{P}_b$, and using the arterial instantaneous blood pressure $\hat{P}_b$ and the diameter displacement change $\Delta \lambda_v$ to make a plot of the arterial dynamic compliance at the critical position.

2. The method of claim 1, wherein the arterial blood vessel diameter change is given by $$\Delta \lambda_s = -1/Z_v \Delta P_b = \Delta \lambda_v.$$

3. The method of claim 1, wherein the arterial instantaneous blood pressure is estimated using the formula $$\hat{P}_b = \overline{P}_b + \Delta P_b = \overline{P}_s - Z_v \Delta \lambda_s.$$

4. The method of claim 1, wherein the arterial dynamic compliance is computed using $$C = [d(\Delta \lambda_s)/d\hat{P}_b]|_{P_b = P_s}.$$

5. The method of claim 1, wherein when the arterial mean blood pressure $\overline{P}_b$ changes by $\Delta \overline{P}_b$ so that the diameter of the arterial blood vessel changes, the actuator urges in the direction opposite to the upper edge of the blood vessel for tracking the mean blood pressure change $\Delta \overline{P}_b$, enabling the detection head at the skin to reach a new critical depth and making the new mean blood pressure $\overline{P}_s$ and the new arterial mean blood pressure $\overline{P}_b$ equal to each other again.

6. The method of claim 5, wherein the actuator increases the depression depth of the skin when the arterial mean blood pressure $\overline{P}_b$ increases so that the blood vessel inflates.

7. The method of claim 5, wherein the actuator reduces the depression depth of the skin when the arterial mean blood pressure $\overline{P}_b$ reduces so that the blood vessel contracts.

8. A device for measuring the arterial instantaneous blood pressure according to the method of claim 1, comprising:
 a detection head disposed on a skin surface, including at least an actuator, a displacement sensor, and a pressure sensor;
 a controlling unit, electrically coupled with the actuator, the displacement sensor, and the pressure sensor for analyzing and processing signals;
 wherein the actuator is controlled by the controlling unit to depress the skin surface; the displacement sensor is used to detect the depression depth of the actuator and send the displacement signal to the controlling unit for signal processing; and the pressure sensor is used to detect the pressure signal at the skin surface and send the pressure signal to the controlling unit for signal processing.

* * * * *